United States Patent

Schuhmacher et al.

[11] Patent Number: 6,159,454
[45] Date of Patent: Dec. 12, 2000

[54] USE OF CHOLESTERIC LIQUID-CRYSTALLINE POLYMERS AS UV SCREENS IN COSMETIC AND PHARMACEUTICAL PREPARATIONS

[75] Inventors: Peter Schuhmacher, Mannheim; Frank Prechtl, Frankfurt, both of Germany

[73] Assignee: BASF Aktiengesellschaft, Ludwigshaften, Germany

[21] Appl. No.: 09/416,895

[22] Filed: Oct. 13, 1999

[30] Foreign Application Priority Data

Oct. 19, 1998 [DE] Germany ............ 198 48 130

[51] Int. Cl.⁷ .............. A61K 7/42; A61K 7/44; A61K 7/00
[52] U.S. Cl. ............ 424/59; 424/60; 424/400; 424/401
[58] Field of Search ............ 424/589, 60, 400, 424/401

[56] References Cited

U.S. PATENT DOCUMENTS

| | | | |
|---|---|---|---|
| 5,747,175 | 5/1998 | Dietz et al. | 428/480 |
| 5,834,064 | 11/1998 | Dietz et al. | 427/388 |
| 5,834,072 | 11/1998 | Schoenfeld et al. | 428/1 |
| 5,837,160 | 11/1998 | Dietz et al. | 252/299 |
| 5,851,277 | 12/1998 | Mueller-Rees et al. | 106/287 |

FOREIGN PATENT DOCUMENTS

| | | |
|---|---|---|
| 199933156 | 12/1999 | Australia . |
| 962222A2 | 12/1999 | European Pat. Off. . |
| 2 586 693 | 6/1987 | France . |
| 19629761 | 8/1997 | Germany . |
| 19612973 | 10/1997 | Germany . |
| 19612974 | 10/1997 | Germany . |
| 19612975 | 10/1997 | Germany . |
| 19620746 | 11/1997 | Germany . |
| 19631658 | 2/1998 | Germany . |
| 19643277 | 4/1998 | Germany . |
| 19738368 | 3/1999 | Germany . |
| 93/22413 | 11/1993 | WIPO . |
| 97/14739 | 4/1997 | WIPO . |

*Primary Examiner*—Shelley A. Dodson
*Attorney, Agent, or Firm*—Keil & Weinkauf

[57] ABSTRACT

Cholesteric liquid-crystalline polymers, especially cholesteric liquid-crystalline polyesters, polycarbonates or polyamides, are used as photostable UV screens in cosmetic and pharmaceutical preparations for protecting the human epidermis or hair against UV radiation, especially in the region from 280 to 450 nm.

12 Claims, No Drawings

USE OF CHOLESTERIC LIQUID-CRYSTALLINE POLYMERS AS UV SCREENS IN COSMETIC AND PHARMACEUTICAL PREPARATIONS

The invention relates to the use of cholesteric liquid-crystalline polymers as photostable UV screens in cosmetic and pharmaceutical preparations for protecting the human epidermis or human hair against UV radiation, especially in the range from 280 to 450 nm.

The function of the photoprotectants (sunscreens) employed in cosmetic and pharmaceutical preparations is to prevent or at least reduce the harmful effects of sunlight on the human skin. In addition, however, these photoprotectants (light stabilizers) also serve to protect other ingredients against destruction or breakdown by UV radiation. In cosmetic formulations for hair the intention is to reduce keratin fiber damage due to UV radiation.

Sunlight reaching the Earth's surface includes a UV-B (from 280 to 320 nm) and a UV-A (>320 nm) radiation fraction which follow on directly from the range of visible light. In the case of UV-B radiation, the effect on human skin is manifested in particular by sunburn. Accordingly, the industry supplies a relatively large number of substances which absorb UV-B radiation and so prevent sunburn.

Dermatological studies have shown that UV-A radiation is also well able to induce skin damage and allergies by causing damage, for example, to the keratin or elastin. This reduces the elasticity and water storage capacity of the skin, which therefore becomes less supple and tends to wrinkle. The extremely high incidence of skin cancer in regions of high solar irradiation shows that sunlight, especially UV-A radiation, apparently induces damage to the inherited information in the cells as well. All of these findings therefore demonstrate the need to develop efficient filter substances for the UV-A and UV-B range.

In addition to the known UV absorbers, such as 2-ethylhexyl 4-methoxycinnamate or 3-(4'-methyl)benzylidenebornan-2-one, the photoprotectants employed in cosmetic and pharmaceutical formulations frequently include those which, in the form of pigments, reflect or absorb the UV rays. The most important of these pigments are titanium dioxide and zinc oxide. At high concentrations, pigments can be used to shield the skin completely. In that case, however, the particles reflect not only UV radiation but also visible light, so leading to the frequently unwanted, strong inherent coloration of pigmented preparations.

Whereas the effect of coarse titanium dioxide pigments (particle size>500 nm) is comparable in the UV-B and UV-A range, the spectrum of action of finely divided material shifts in the UV-B direction as the particle size decreases. This shows that the absorption/reflection characteristics are directly dependent on the size and distribution of the particles. Balanced UV-B and UV-A protection therefore requires specific particle size distributions.

A disadvantage when using the abovementioned pigments is that the storage of the cosmetic or pharmaceutical photoprotectant formulations is often accompanied by agglomeration, aggregation and/or separation of the pigment particles. The change in optical properties which this brings about may result in a drastically reduced photoprotective effect.

As an alternative to the abovementioned pigments DE-A-196 19 460 describes the use of liquid-crystal mixtures with a cholesteric phase comprising a) liquid-crystalline organosiloxanes comprising dianhydrohexitol derivatives as chiral groups and b) chiral monomeric additives which induce the same helical twist as the respective liquid-crystalline organosiloxanes for preparing UV protective layers in the form of films or platelets which are suitable for cosmetic purposes. The liquid-crystal mixtures described therein have the drawback of their high viscosity, which makes them difficult to process satisfactorily to pigments.

DE-A-196 29 761 describes cosmetic or pharmaceutical preparations comprising goniochromatic polyorganosiloxane pigments. The pigments comprise at least one oriented crosslinked substance having a liquid-crystalline structure with a chiral phase. The pigments disclosed in the cosmetic and pharmaceutical formulations here, although possessing certain absorption properties in the UV range, have the drawback for certain applications that they are colored compounds whose field of use is limited as a result. Very frequently, however, the demand is for cosmetic and pharmaceutical preparations which achieve UV protection but in which any coloration is unwanted.

Further cholesteric liquid-crystalline polymers, again colored and goniochromatic, are described, inter alia, in DE-A-196 31 45 658, DE-A-196 43 277, DE-A-196 12 973, DE-A-196 12 974, DE-A-196 12 975, DE-A-196 20 746 and in WO 97/14739.

It is an object of the present invention to propose new photoprotectants for cosmetic and pharmaceutical purposes which act as screens in the UV-A and/or UV-B range and which, in the form of pigments, do not have the disadvantages set out above.

We have found that this object is achieved in accordance with the invention by the use of cholesteric liquid-crystalline polymers whose main chains comprise alternately the structural element —X—C(=O)— in which X is oxygen or NH as UV screens in cosmetic and pharmaceutical preparations for protecting the human skin or hair against the sun's rays, alone or together with UV absorbers known per se for cosmetic and pharmaceutical preparations.

The structural element —X—C(=O)— here forms the linkage site within the polymer chain and can be, inter alia, an ester, carbonate, amide or carbamate group.

Preference is given to cholesteric main-group polymers composed of the following structural units of the individual monomer groups:

a) at least one chiral bifunctional molecular structural unit with which a cholesteric liquid-crystalline phase having a pitch of less than 450 nm can be obtained and at least one further molecular unit selected from b) achiral compounds from the group consisting of aromatic hydroxycarboxylic acids, cycloaliphatic hydroxycarboxylic acids, aromatic aminocarboxylic acids and cycloaliphatic aminocarboxylic acids;

c) achiral compounds from the group consisting of aromatic dicarboxylic acids and cycloaliphatic dicarboxylic acids, and d) achiral compounds from the group consisting of aromatic diols, cycloaliphatic diols, aromatic diamines and cycloaliphatic diamines.

Particular preference is given to cholesteric main-group polymers comprising a) from 1 to 60 mol %, preferably from 3 to 50 mol %, of at least one chiral, bifunctional molecular unit;

b) from 0 to 99 mol %, preferably from 5 to 90 mol %, of at least one achiral unit from the group consisting of aromatic hydroxycarboxylic acids, cycloaliphatic hydroxycarboxylic acids, aromatic aminocarboxylic acids and cycloaliphatic aminocarboxylic acids;

c) from 0 to 49.5 mol %, preferably from 0 to 40 mol %, of at least one achiral unit from the group consisting of aromatic dicarboxylic acids and cycloaliphatic dicarboxylic acids, and d) from 0 to 99 mol %, preferably from 0 to 49.5 mol %, of at least one achiral unit from the group consisting of aromatic diols, cycloaliphatic diols, aromatic diamines and cycloaliphatic diamines, e) from 0 to 5 mol % of a branchable component having more than two functional groups, the sum of the individual components a) to e) being 100 mol %.

The components of group a) are judiciously recruited from the chiral pool. By this is meant in the art (Ullmanns Encycl. Techn., 5th Edition, Vol. A18, p. 183, 1991, VCH-Verlag) the entirety of naturally occurring chiral compounds. The pool includes in particular chiral structural units of both animal and vegetable origin. However, this by no means excludes the use of fully or partly synthetic chiral molecular structural units. For instance, natural substances can be subjected to one or more synthesis steps to give valuable chiral components which in the synthesized form do not occur in nature or do so only in small amounts.

Particularly suitable molecular structural units a), generally speaking, are all chiral, bifunctional components, examples being chiral diols and polyols, chiral dicarboxylic acids, chiral hydroxycarboxylic acids and aminocarboxylic acids.

Preferred representatives of group a) are the following compounds:

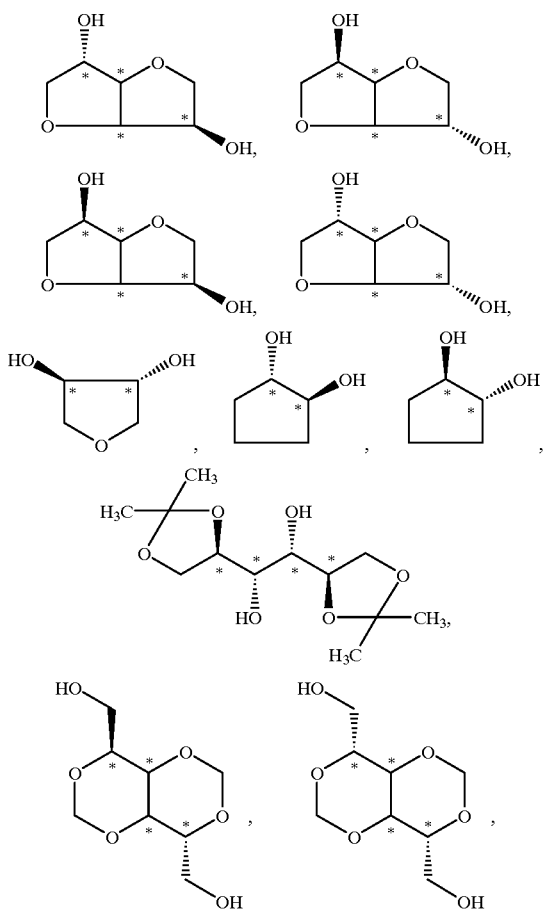

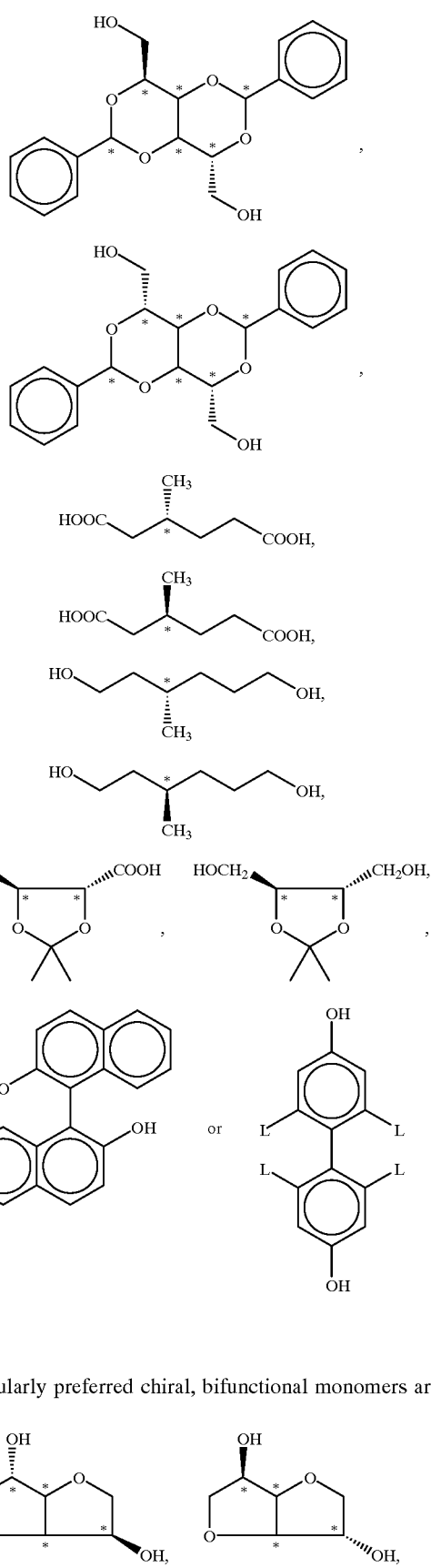

Particularly preferred chiral, bifunctional monomers are:

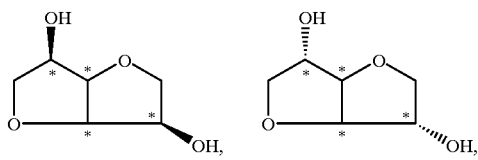
The chiral comonomers are preferably employed in an enantiomerically pure form. When using enantiomer mixtures of a comonomer, it should be ensured that one enantiomeric form is in an effective excess.
Preferred components b) are:
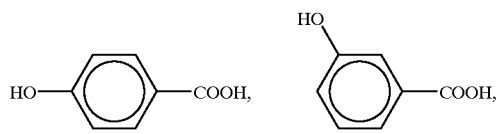
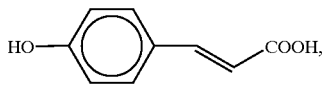
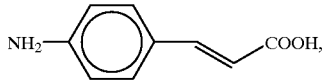
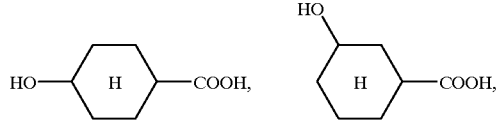
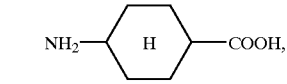
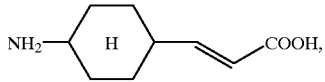
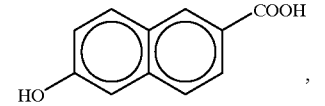
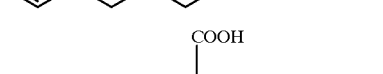
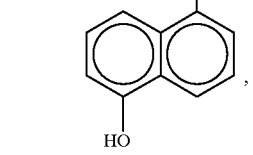
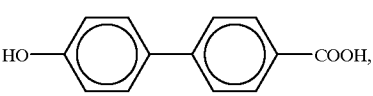
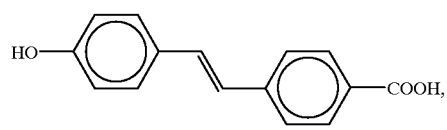
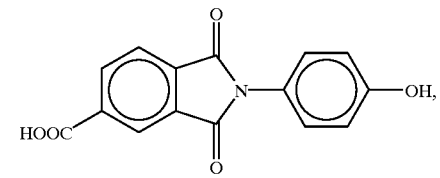
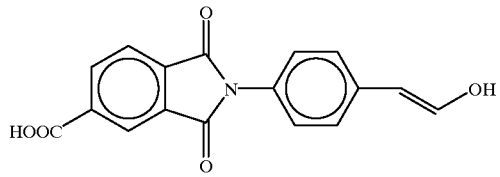
Particularly preferred representatives of group b) are:
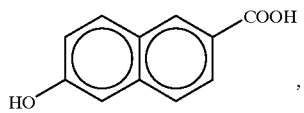
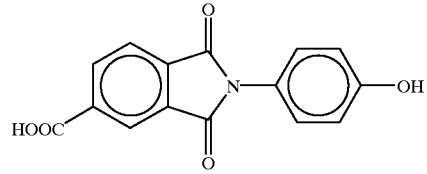
Preferred components c) are:
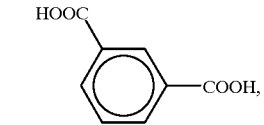
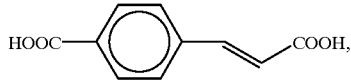
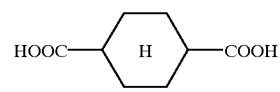
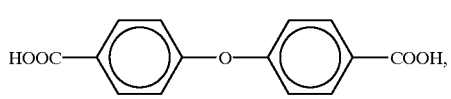

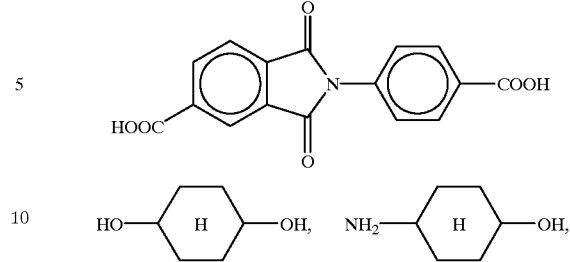
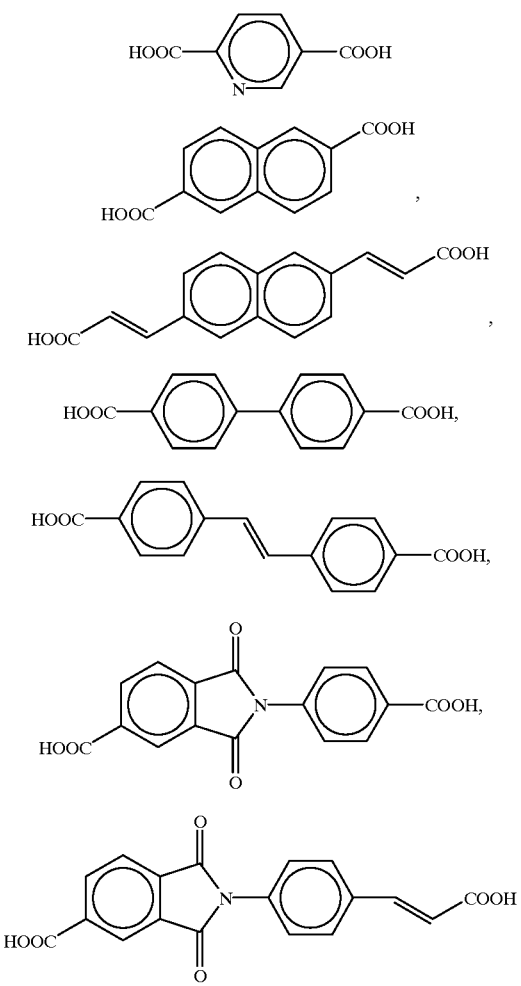
Particularly preferred representatives of group c) are:
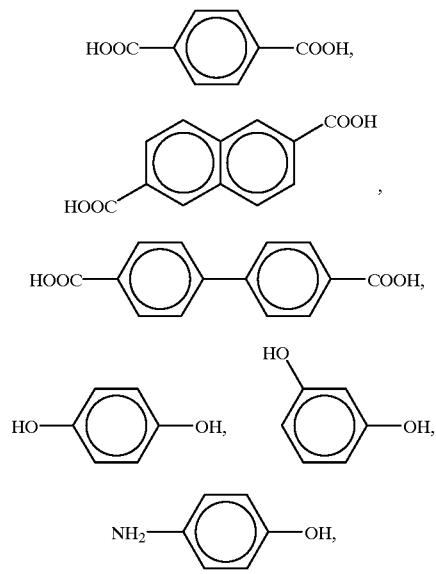
Preferred components d) are:
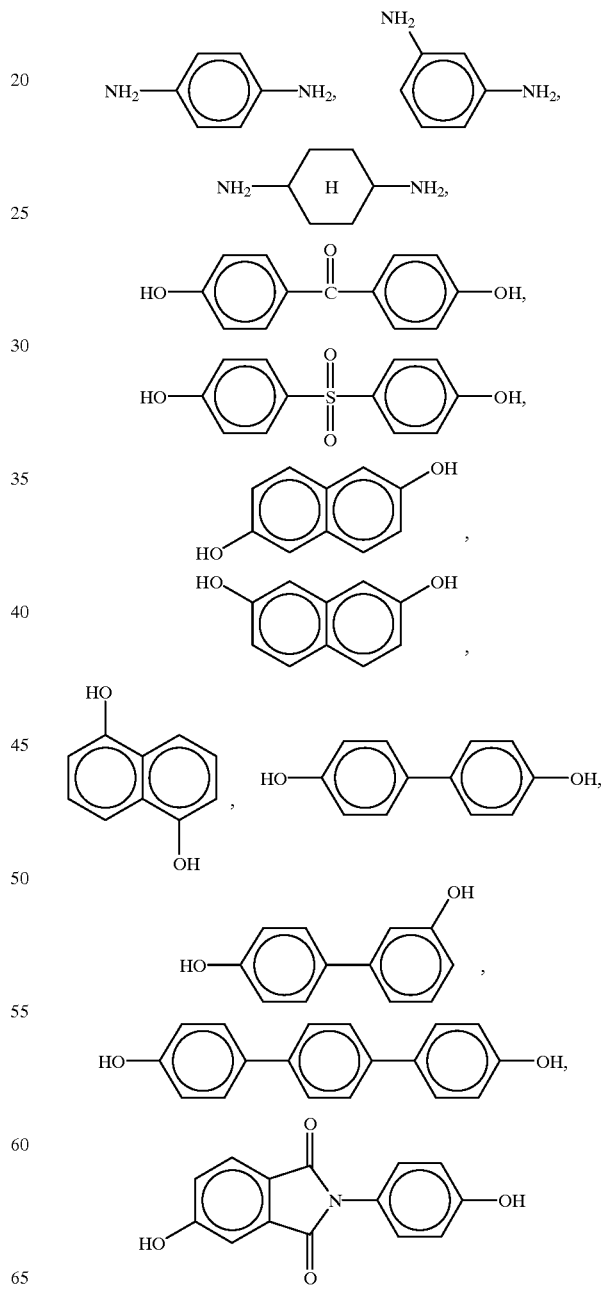

Particularly preferred representatives of group d) are:

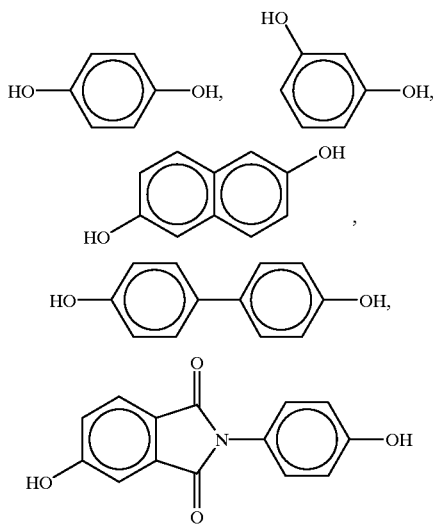

Instead of the carboxylic acids it is further possible to employ carboxylic acid derivatives which are known to the skilled worker, such as carbonyl chlorides, carboxylic anhydrides or carboxylic esters, for example. Instead of the hydroxy components it is also possible to employ corresponding hydroxy derivatives, such as the acylated hydroxy compounds, for example.

In addition the polymers may include components having more than two functional groups, such as dihydroxybenzoic acid or trihydroxybenzenes, for example. These components act as branching sites in the polymer and are added if at all in only small concentrations, such as from 0 to 5 mol %.

The polymers used in accordance with the invention can be prepared by various modes of polycondensation or by transesterification of polyesters with a mixture comprising acid component and acylated alcohol component.

Customary polycondensation methods for the polyesters, which are used preferably, are, for example, the HCl, the silyl and the transesterification technique. These techniques are known inter alia from H. R. Kricheldorf, N. Probst; Makromol. Rapid. Commun. (1995) 16, 231 and N. Probst, H. R. Kricheldorf; High Perform. Polym. (1995) 7, 461.

The acid and alcohol components are employed in a molar ratio of approximately 1:1.

The reaction time may vary widely. It is generally from 1 to 48 h, in particular from 1 to 24 h.

The reaction is conducted at elevated temperature, generally in the range from 120° C. to 300° C., and within this range the temperature may also be increased in steps.

In the HCl method the free diols are dissolved with the dichlorides of the dicarboxylic acids in an appropriate organic solvent, for example, an ether such as dioxane or a chlorinated hydrocarbon such as 1,1,2,2-tetrachloroethane, 1-chloronaphthalene or 1,2-dichlorobenzene, in a suitable reaction vessel. An example of a suitable reaction vessel is a pressure-resistant stirred vessel with gas inlet and outlet lines.

Preferably, the hydrogen chloride liberated is removed in a gentle stream of nitrogen. The polyester obtained is dried at elevated temperature, for instance at about 120° C., under reduced pressure. If desired, the polyester is subjected to a purification step by redissolving it in one of the abovementioned solvents and precipitating it from methanol.

If the polymer is soluble in the solvent used the organic phase is separated off and the polyester is recovered from it in a conventional manner: for example, by taking it up in methanol and isolating it by filtration. If, on the other hand, the polymer precipitates from the solvent or there is gelling, the reaction mixture is diluted if appropriate, with methanol, for example, and the polymer is isolated by filtration.

In the case of the silyl method the bissilylated diols are heated with the dichlorides of the dicarboxylic acids in the presence of a catalytic amount of a quaternary ammonium salt such as triethylbenzylammonium chloride, for example, in bulk or with one of the abovementioned solvents in a suitable reaction vessel as described above. The resultant polyester is worked up as described above.

In the case of the transesterification method the free dicarboxylic acids are reacted with the acetylated diols in bulk in the presence of catalytic amounts of an alkali metal oxide or alkaline earth metal oxide (MgO, for example) or in the presence of zinc, tin, zirconium, manganese and bismuth salts in a suitable reaction vessel as described above. The resultant polyester is worked up as described above.

In the transesterification of a polyester (A) with free dicarboxylic acid (B) and acetylated diol (C) the reactants are employed in a molecular mass ratio A:B:C of from about 1 to 5:1 to 5:1 to 5, in particular about 1:2:2. The reaction is conducted in a suitable reaction vessel in the presence, preferably, of catalytic amounts of an early transition metal alkylate, e.g., titanium tetrabutylate. The reaction vessel is preferably flushed with nitrogen several times in order to remove air. The acetic acid released during the reaction is preferably removed in a gentle stream of nitrogen. The reaction is preferably continued under reduced pressure.

Of the abovementioned preparation methods, the HCl method, the silyl method and transesterification are particularly preferred.

The preparation of the polycarbonates having carbonate units which comprise a mesogenic group and carbonate units which comprise a chiral group, the said polycarbonates being used in accordance with the invention and likewise preferred, can be carried out by various types of polycondensation of diols of group a) and d) with phosgene or diphosgene. Components a) and d) are employed in the molar ratio of from 1:1 to 1:10,000, preferably from 1:1 to 1:1000. Examples of common types of polycondensation are interface polycondensation, melt polycondensation and solution polycondensation.

In the case of interface polycondensation the diols comprising the mesogenic group, the chiral group and, if desired, a photoreactive group are dissolved together with phosgene or, preferably, the substantially less hazardous diphosgene or triphosgene and a catalytic amount of an amine, such as triethylamine, or a quaternary ammonium salt, such as triethylbenzylammonium chloride, in an appropriate organic solvent, for example, an ether such as tetrahydrofuran or dioxane, or a chlorinated hydrocarbon such as dichloromethane or chlorobenzene. An aqueous base, such as sodium hydroxide solution, is added to this solution and the two phases are mixed with one another by means, for example, of vigorous stirring. Cooling is preferably carried out during the stirring operation. If the polymer is soluble in the solvent used the organic phase is separated off and the polycarbonate is recovered from it conventionally by, for example, taking it up in methanol and isolating it by filtration. If, on the other hand, the polymer precipitates from the solvent or there is gelling, the reaction mixture is diluted if desired, with methanol, for example, and the polymer is isolated by filtration. Alternatively to phosgene or diphosgene it is also possible to employ the chlorinated dicarbonates of the diols that are to be condensed.

In the case of melt polycondensation the dicarbonate of one of the diols forming the mesogenic group, the chiral group and, if desired, the photoreactive group is reacted with the diols forming the remaining groups. The reaction is conducted at a relatively high temperature, generally in the range from 120° C. to 300° C., and within this range the temperature can also be increased in steps. The resultant polymer is dissolved or suspended in one of the abovementioned appropriate solvents and is precipitated with methanol is desired.

In the case of solution polycondensation the diols forming the mesogenic group, the chiral group and, if desired, the further, nonchiral group and the photoreactive group are dissolved in an amine, preferably a tertiary or aromatic amine, an example being pyridine. To this solution there is added diphosgene dissolved in one of the abovementioned appropriate solvents. The reaction temperature is generally in the range from about 0° C. to ambient but may even be higher for the purpose, in particular, of completing the reaction. The mixture is then worked up conventionally. In the solution polycondensation, alternatively to the use of diphosgene, it is also possible to use the chlorinated dicarbonates of the diols that are to be polymerized.

Of the condensation methods referred to, preference is given to interface polycondensation and solution polycondensation, the latter especially when using relatively hydrophilic monomers such as isosorbide, for example, which in the case of interface polycondensation transfer much less well from the aqueous to the organic phase than do the other monomers with which they are to be condensed.

If the cholesteric liquid-crystalline polymers are not already fine powders in the as-synthesized form, then they must be converted to corresponding fine powders following polymerization.

To this end an appropriate first comminution step following synthesis is extrusion as a strand or strip. The resultant strands or strips can be converted conventionally into chips or strand pellets using choppers or pelletizers.

Conventional milling equipment of all kinds and embodiments is appropriate for further comminution.

For the use of the abovementioned cholesteric liquid-crystalline polymers as UV screens in cosmetic and pharmaceutical preparations, in accordance with the invention, they can be incorporated directly into the cosmetic and pharmaceutical preparations.

Preferably, however, the cholesteric liquid-crystalline polymers used in accordance with the invention are employed in the form of pigments.

There are a number of options for preparing cholesteric pigments:

1) Solution coating. In this case the polymer is dissolved in a solvent and applied from solution as a film to a substrate such as a film, metal strip or metal roller. This can be done, for example, by spraying, knife coating, pouring, dipping or brushing. After the solvent has evaporated the polymer forms a UV-reflective layer on the substrate.

2) Melt coating. In this case the polymer in the melt is applied to the substrate or is melted on the substrate and processed to form a thin layer.

3) Powder coating. In this case the polymer is ground in one step to the desired particle size using known milling equipment. Subsequently, the powder is applied by known methods such as, for example, the flame spraying method.

During or after the process of application to the substrate, the powder layer is heated to temperatures above the softening point of the polymer. In the course of heating the polymers form a homogeneous film in which the helical superstructures develop. The temperature at which the development of the helical structure begins is referred to below as the chiralization temperature.

The UV pigments can be prepared, for example, by detaching the oriented polymer film from the coated surface and milling it to form platelet-shaped pigments, or by appropriate milling of the extruded polymer strands.

The special UV-reflective properties of the pigments used in accordance with the invention are observed only when, above the chiralization temperature of the polymer, the molecules develop the helical structures. In many cases transition to the cholesteric phase takes place even during the synthesis of the polymers. The wavelength of the selective reflection of the polymers used in accordance with the invention is determined by the pitch of the helical structure. The pitch is dependent on the structure of the polymers and on the twisting power of the chiral monomer. It is also a function of temperature. Accordingly, the pitch of the helix can also be adjusted by way of the temperature. Rapid cooling of the coated substrates enables the pitch of the helix, and thus the selective reflection, to be frozen in permanently. For use in practice it is important that the melting point and the chiralization temperature of the polymer lie above the service temperature of the pigment.

Where the polymer comprises photocrosslinkable groups, the UV-reflectibe structure of the polymer can also be fixed by photochemical crosslinking of the chiral nematic phase.

Depending on the desired use, and on the nature of the cosmetic or pharmaceutical formulation, particle sizes having a diameter of from 1 to 1000 mm can be prepared. Preferably particle sizes are within the range from 1 to 100 mm, and, with particle preference, from 15 to 50 mm.

The thickness of the pigments from 1 to 100 mm, preferably from 1 to 50 mm and, with particular preference, from 1.5 to 10 mm.

An overview of techniques of crosslinking oriented starting materials photochemically is given in C. G. Roffey, Photopolymerisation of Surface Coatings (1982), John Wiley & Sons, Chichester, pp. 137 to 208.

The cholesteric liquid-crystalline polymers suitable as starting substances for preparing the pigments possess a twisted structure with a pitch that corresponds to a wavelength of light up to 450 nm. The nature and proportion of the chiral substance determine the pitch of the twisted structure and thus the wavelength of the reflected light. Depending on the chirality of the optically active additives that are employed, the twisting of the structure may be either left or right handed.

Broadband reflectors, as they are known, can be produced simply by mixing two or more of the cholesteric liquid-crystalline pigments to be used in accordance with the invention, each having different UV reflection maxima.

It is possible, furthermore, to obtain complete reflection of UV rays by mixing at least two different pigments of cholesteric liquid-crystalline polymers each with opposite twist (helicity). Pigments of such cholesteric liquid-crystalline structures each with opposite twist are obtainable, for example, by adding in each case the individual mirror-image isomers (enantiomers) or diastereomers of the chiral monomers a) to the achiral polymerizable monomers b–d). In this context, the pitch of the structures each with opposite twist can be the same or different.

It is also possible to mix the cholesteric liquid-crystalline polymers each of opposite twist first of all, then to convert them into the pigments already described above and to employ said pigments as UV reflectors in cosmetic and pharmaceutical formulations.

In addition to the abovementioned mixtures of cholesteric liquid-crystalline pigments it is also possible to produce multilayer pigments whose individual layers comprise different representatives of the cholesteric liquid-crystalline polymers to be used in accordance with the invention. The design possibilities for such multilayer pigments are diverse. They include, for instance individual layers of cholesteric liquid-crystalline polymers of opposite twist or individual layers of cholesteric liquid-crystalline polymers with the same twist sense but different pitch and therefore different reflection properties applied over one another.

Preference is given to three-layer pigments in which the two outer layers consist of one each of the cholesteric liquid-crystalline polymers to be used in accordance with the invention and the middle layer may, for example, comprise a binder matrix in which a further UV absorber may additionally be incorporated. Particulars of the preparation, properties and further constituents of such multilayer cholesteric pigments are given in German Patent Application P 19738368.8.

Particular preference is given to two-layer pigments, in which the two layers consist of one each of the cholesteric liquid-crystalline polymers to be used in accordance with the invention, these pigments being prepared by coextrusion.

The invention therefore also provides the pigments described above, especially multilayer pigments, comprising the cholesteric liquid-crystalline polymers specified at the beginning.

An advantage of the pigments used in accordance with the invention is that their composition can be tailored to the desired UV reflection without having any inherent coloration (in the visible range).

A further advantage of the pigments lies in their physical properties. Because of their low density (in comparison, for example, to $TiO_2$) the pigments lend themselves well to incorporation into emulsions without aggregation or separation of the pigment particles.

The pigments to be used in accordance with the invention can be incorporated into the cosmetic and pharmaceutical preparations by simple blending.

The present invention additionally provides cosmetic and pharmaceutical preparations which comprise from 0.1 to 20% by weight, preferably from 0.5 to 10% by weight and, with particular preference, from 1 to 7% by weight, based on the overall amount of the cosmetic and pharmaceutical preparation, of one or more of the cholesteric liquid-crystalline polymers whose main chains comprise alternately the structural element —X—C(=O)— in which X is oxygen or NH together with compounds which are known per se for cosmetic and pharmaceutical preparations and which absorb in the UV-A and UV-B region as photoprotectants. The polymers, and the class of substance comprising the chiral and achiral monomers employed, correspond here to the definitions already set out above, both in a general embodiment and in their preferred embodiment.

Preference is given to those of the abovementioned cosmetic and pharmaceutical preparations which comprise the cholesteric liquid-crystalline polymers to be used in accordance with the invention in the form of the pigments already described, especially in the form of multilayer pigments.

The cosmetic and pharmaceutical preparations comprising photoprotectants are generally based on a carrier which comprises at least one oil phase. However, preparations based solely on water are also possible when using compounds having hydrophilic substituents. Accordingly, oils, oil-in-water and water-in-oil emulsions, cosmetic creams and pastes, protective lipstick bases or nongreasy gels are suitable.

Sun protection preparations of this kind can accordingly be in liquid, pastelike or solid form, for example, as water-in-oil creams, oil-in-water creams and lotions, aerosol foam creams, gels, oils, grease sticks, dusting powders, sprays or hydroalcoholic lotions.

Examples of customary oil components in cosmetics are liquid paraffin, glyceryl stearate, isopropyl myristate, diisopropyl adipate, stearyl 2-ethylhexanoate, hydrogenated polyisobutene, vaseline, caprylic/capric triglycerides, microcrystalline wax, lanolin and stearic acid.

Customary cosmetic auxiliaries which may be suitable as additives are, for example, coemulsifiers, fats and waxes, stabilizers, thickeners, biogenic active substances, film formers, fragrances, dyes, pearlescent agents, preservatives, pigments, electrolytes (e.g., magnesium sulfate) and pH regulators. Suitable coemulsifiers are preferably known W/O and O/W emulsifiers, such as polyglyceryl esters, sorbitan esters or partially esterified glycerides. Typical examples of fats are glycerides; waxes which may be mentioned include beeswax, paraffin wax or microwaxes, alone or in combination with hydrophilic waxes. Stabilizers which can be employed are metal salts of fatty acids such as magnesium, aluminum and/or zinc stearate. Examples of suitable thickeners are crosslinked polyacrylic acids and their derivatives, polysaccharides, especially xanthan gum, guar-guar, agar-agar, alginates and Tyloses, carboxymethylcellulose and hydroxyethylcellulose, and also fatty alcohols, monoglycerides and fatty acids, polyacrylates, polyvinyl alcohol and polyvinylpyrrolidone. By biogenic active substances are meant, for example, plant extracts, protein hydrolysates and vitamin complexes. Examples of film formers which are in use are hydrocolloids such as chitosan, microcrystalline chitosan or quaternized chitosan, polyvinylpyrrolidone, vinylpyrrolidone-vinyl acetate copolymers, polymers of the acrylic acid series, quaternary cellulose derivatives and similar compounds. Examples of suitable preservatives are formaldehyde solution, p-hydroxybenzoate or sorbic acid. Examples of suitable pearlescent agents are glycol distearic esters such as ethylene glycol distearate, but also fatty acids and fatty acid monoglycol esters. Dyes which can be used are the substances suitable and approved for cosmetic purposes, as tabulated, for example, in the publication "Kosmetische Farbemittel" of the Farbstoffkommission der Deutschen Forschungsgemeinschaft, published by Verlag Chemie, Weinheim 1984. These dyes are normally employed in a concentration of from 0.001 to 0.1% by weight, based on the overall mixture.

If desired, the preparations of the invention may also include one or more antioxidants. Antioxidants favorable for use, but nevertheless optional, can be all natural, synthetic and/or partially synthetic antioxidants which are commonly in use or suitable for cosmetic and/or dermatological applications.

With particular advantage, the antioxidants are chosen from the group consisting of:

amino acids (e.g. glycine, histidine, tyrosine and tryptophan) and their derivatives, imidazoles (e.g. urocanic acid) and their derivatives, peptides such as D,L-carnosine, D-carnosine, L-carnosine and their derivatives (e.g. anserine), carotinoids (e.g. β-carotene, lycopene) and their derivatives, liponic acid and its derivatives (e.g. dihydroliponic acid), aurothioglucose, propylthiouracile and other thio compounds (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and salts thereof, dilauryl thiodipropionate, distearyl thiodipropionate, thiodipropionic acid and its derivatives (esters, ethers, peptides, lipids, nucleotides, nucleosides and salts) and also sulfoximine compounds (e.g. buthionine sulfoximine, homocysteine sulfoximine, buthionine sulfones, penta-, hexa- and heptathionine sulfoximine) in very low tolerated dosages (e.g. pmol to $\mu$mol/kg), and also (metal) chelating agents (e.g. α-hydroxy fatty acids, palmitic acid, phytic acid, lactoferrin), α-hydroxy acids (e.g. citric acid, lactic acid, maleic acid), humic acid, bile acid, bile extracts, bilirubin, biliverdin, EDTA, EGTA and their derivatives, unsaturated fatty acids and their derivatives (e.g. γ-linolenic acid, linoleic acid, oleic acid), folic acid and its derivatives (e.g. 5-methyltetrahydrofolic acid), ubiquinone and ubiquinole and their derivatives, vitamin C and its derivatives (e.g. ascorbyl palmitate, ascorbyl phosphates, ascorbyl acetates), tocopherols and derivatives (e.g. tocopheryl acetate, tocotrienol), vitamin A and derivatives (e.g. vitamin A palmitate), rutic acid and its derivatives, ferulic acid and its derivatives, butylated hydroxytoluene, butylated hydroxyanisole, nordihydroguaiac resin acid, nordihydroguaiaretic acid, trihydroxybutyrophenone, uric acid and its derivatives, stilbenes and their derivatives.

The overall proportion of auxiliaries and additives can be from 1 to 80, preferably 6 to 40, % by weight and the nonaqueous fraction (active substance) can be from 20 to 80, preferably 30 to 70, % by weight—based on the preparation. The preparation can be produced in a manner known per se, i.e., for example, by hot, cold, hot/cold or PIT emulsification. This is a purely mechanical process; no chemical reaction takes place.

Finally, it is also possible to use other substances which absorb in the UV region and are known per se provided they are stable in the overall system of the combination of UV screens to be used in accordance with the invention.

The majority of the photoprotectants in the cosmetic and pharmaceutical preparations used to protect the human epidermis consists of compounds which absorb UV light in the UV-B region, i.e., in the region from 280 to 320 nm. For example, the proportion of cholesteric liquid-crystalline compositions to be used in accordance with the invention is from 10 to 90% by weight, preferably from 20 to 70% by weight, based on the overall amount of UV-B- and UV-A-absorbing substances.

Suitable UV filter substances employed in combination with the cholesteric liquid-crystalline compositions to be used in accordance with the invention are any desired UV-A and UV-B filter substances. Examples are:

| No. | Substance | CAS No. (=Acid) |
|---|---|---|
| 1 | 4-Aminobenzoic acid | 150-13-0 |
| 2 | 3-(4'-Tnmethylammonium)berzylidenebornan-2-one methyl sulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxobicyclo[2.2.1]heptane-1-methanesulfonic acid) and its salts | 90457-82-2 |
| 7 | polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and the sodium salt | 4065-45-6 |
| 13 | 3-(4'-Methyl)benzylidenebornan-2-one | 36861-47-9 |
| 14 | 3-Benzylidenebornan-2-one | 15087-24-8 |
| 15 | 1-(4'-Isopropylphenyl)-3-phenylpropane-1,3-dione | 63250-25-9 |
| 16 | 4-Isopropylbenzyl salicylate | 94134-93-7 |
| 17 | 2,4,6-Trianilino(o-carbo-2'-ethylhexyl-1'-oxy)-1,3,5-triazine | 88122-99-0 |
| 18 | 3-(4-Imidazolyl)acrylic acid and its ethyl ester | 104-98-3 |
| 19 | Ethyl 2-cyano-3,3-diphenylacrylate | 5232-99-5 |
| 20 | 2-Ethylhexyl 2-cyano-3,3-diphenylacrylate | 6197-30-4 |
| 21 | Menthyl o-aminobenzoate or: 5-methyl-2-(1-methylethyl)cyclohexyl 2-aminobenzoate | 134-09-8 |
| 22 | Glyceryl p-aminobenzoate or: 4-aminobenzoic acid 1-glyceryl ester | 136-44-7 |
| 23 | 2,2'-Dihydroxy-4-methoxybenzophenone (dioxybenzone) | 131-53-3 |
| 24 | 2-Hydroxy-4-methoxy-4-methylbenzophenone (mexonone) | 1641-17-4 |
| 25 | Triethanolamine salicylate | 2174-16-5 |
| 26 | Dimethoxyphenylglyoxalic acid or: sodium 3,4-dimethoxyphenylglyoxalate | 4732-70-1 |
| 27 | 3(4'-Sulfo)benzylidenebornan-2-one and its salts | 56039-58-8 |
| 28 | 4-tert-Butyl-4'-methoxydibenzoylmethane | 70356-09-1 |
| 29 | 2,2',4,4'-Tetrahydroxybenzophenone | 131-55-5 |
| 30 | Dimethicone diethylbenzalmalonate | 207574-74-1 |
| 31 | Bis[2-hydroxy-5-tert-octyl-3-(benzotriazol-2-yl)phenyl]methane (bisoctyltrialone) | 103597-45-1 |

-continued

| No. | Substance | CAS No. (=Acid) |
|---|---|---|
| 32 | 1H-Benzimidazole-4,6-disulfonic acid 2,2'-(1,4-phenylene)bis-disodium salt (benzimidazylate) | 180898-37-7 |
| 33 | 2,2'-[6-(4-Methoxyphenyl)-1,3,5-triazin-2,4-diyl]bis[5-[(2-ethyl-hexyl)oxy]phenol (anisotriazine) | 187393-00-6 |

Finally, mention may also be made of micronized pigments such as titanium dioxide and zinc oxide.

To protect human hair against UV rays the cholesteric liquid-crystalline polymers used in accordance with the invention can be incorporated into shampoos, lotions, gels, hair sprays, aerosol foam creams or emulsions in concentrations of from 0.1 to 20% by weight, preferably from 0.5 to 10% by weight and, with particular preference, from 1 to 7% by weight. The respective formulations can be used inter alia for washing, coloring and setting the hair.

The compositions to be used in accordance with the invention generally feature a particularly high reflectance in the region of UV-A and UV-B radiation, with a sharp band structure. Furthermore, they are easy to incorporate into cosmetic and pharmaceutical formulations. In addition, they are notable in particular for their high photostability, and the preparations produced with them are notable for their pleasant feel to the skin.

The UV screening (filter effect) of the cholesteric liquid-crystalline polymers used in accordance with the invention can also be utilized to stabilize active substances and auxiliaries in cosmetic and pharmaceutical formulations.

The subject matter of the present invention will be elucidated on the basis of the following examples.

EXAMPLE 1

19,665 parts of 2-hydroxy-6-naphthoic acid, 24,067 parts of 4-hydroxybenzoic acid, 18,343 parts of terephthalic acid, 93 parts of 4,4'-dihydroxybiphenyl and 16,060 parts of 1,4:3,6-dianhydro-D-sorbitol (isosorbide) were admixed in the reactor with 52,680 parts of acetic anhydride and the mixture was flushed with a gentle stream of nitrogen. The mixture was heated to 140° C. over the course of 15 minutes with stirring and this temperature was maintained for 30 minutes. Thereafter, the temperature was raised to 325° C. over the course of 165 minutes and the melt was stirred further at this temperature for 30 minutes. From about 220° C., acetic acid began to distill off. Thereafter, the nitrogen flushing was broken off and reduced pressure was applied slowly. The melt was stirred under reduced pressure (about 5 mbar) for a further 30 minutes. Thereafter, it was vented with nitrogen and the polymer was discharged using an extruder and pelletized. Reflectance measurements show a band in the UV region.

Formulations

EXAMPLE 2

Lipcare composition
Content by mass
(% by weight)

| | |
|---|---|
| ad 100 | eucerinum anhydricum |
| 10.00 | glycerol |
| 5.00 | pigment of polymer from Example 1 |
| 8.00 | octyl methoxycinnamate |
| 5.00 | zinc oxide |
| 4.00 | castor oil |
| 4.oo | pentaerythrityl stearate/caprate/caprylate adipate |
| 3.00 | glycerol stearate SE |
| 2.00 | beeswax |
| 0.50 | tocopheryl acetate |
| 2.00 | microcrystalline wax |
| 2.00 | quaternium-18 bentonite |
| 1.50 | PEG-45/dodecyl glycol copolymer |

EXAMPLE 3

Composition for sunblock with micropigments
Content by mass
(% by weight)

| | |
|---|---|
| ad 100 | water |
| 10.00 | octyl methoxycinnamate |
| 6.00 | PEG-7 hydrogenated castor oil |
| 6.00 | titanium dioxide |
| 5.00 | pigment of polymer from Example 1 |
| 5.00 | mineral oil |
| 5.00 | isoamyl p-methoxycinnamate |
| 5.00 | propylene glydol |
| 3.00 | jojoba oil |
| 3.00 | 4-methylbenzylidenecamphor |
| 2.00 | PEG-45/dodecyl glycol copolymer |
| 1.00 | dimethicone |
| 0.50 | PEG-40 hydrogenated castor oil |
| 0.50 | tocopheryl acetate |
| 0.50 | phenoxyethanol |
| 0.20 | EDTA |

EXAMPLE 4

Nongreasy gel
Content by mass
(% by weight)

| | |
|---|---|
| ad 100 | water |
| 8.00 | octyl methoxycinnamate |
| 5.00 | pigment of polymer from Example 1 |
| 5.00 | glycerol |
| 5.00 | PEG-25 PABA |

-continued

| | |
|---|---|
| 1.00 | 4-methylbenzylidenecamphor |
| 0.40 | acrylate C10–C30 alkyl acrylate crosspolymer |
| 0.30 | imidazolidinylurea |
| 0.25 | hydroxyethylcellulose |
| 0.25 | sodium methylparaben |
| 0.20 | disodium EDTA |
| 0.15 | fragrance |
| 0.15 | sodium propylparaben |
| 0.10 | sodium hydroxide |

EXAMPLE 5

Suncream (SPF 20)
Content by mass
(% by weight)

| | |
|---|---|
| ad 100 | water |
| 8.00 | octyl methoxycinnamate |
| 6.00 | PEG-7 hydrogenated castor oil |
| 5.00 | pigment of polymer from Example 1 |
| 6.00 | mineral oil |
| 5.00 | zinc oxide |
| 5.00 | isopropyl palmitate |
| 5.00 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | disodium EDTA |
| 0.15 | propylparaben |

EXAMPLE 6

Water resistant suncream
Content by mass
(% by weight)

| | |
|---|---|
| ad 100 | water |
| 8.00 | octyl methoxycinnamate |
| 5.00 | PEG-7 hydrogenated castor oil |
| 5.00 | propylene glycol |
| 4.00 | isopropyl palmitate |
| 4.00 | caprylic/capric triglyceride |
| 5.00 | pigment of polymer from Example 1 |
| 4.00 | glycerol |
| 3.00 | jojoba oil |
| 2.00 | 4-methylbenzylidenecamphor |
| 1.50 | PEG-45/dodecyl glycol copolymer |
| 1.50 | dimethicone |
| 0.70 | magnesium sulfate |
| 0.50 | magnesium stearate |
| 0.50 | tocopheryl acetate |
| 0.15 | fragrance |

EXAMPLE 7

Sunmilk (SPF 6)
Content by mass
(% by weight)

| | |
|---|---|
| ad 100 | water |
| 10.00 | mineral oil |
| 6.00 | PEG-7 hydrogenated castor oil |

-continued

| | |
|---|---|
| 5.00 | isopropyl palmitate |
| 3.50 | octyl methoxycinnamate |
| 3.00 | pigment of polymer from Example 1 |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 0.30 | glycerol |
| 0.25 | methylparaben |
| 0.15 | propylparaben |

We claim:

1. A method of protecting human skin or human hair from the rays of the sun which comprises applying an effective amount of at least one cholesteric liquid-crystalline polymer whose main chains comprise alternately the structural element —X—C(=O)— in which X is oxygen or NH as UV screens.

2. A method as claimed in claim 1, wherein said polymers are cholesteric liquid-crystalline polyesters, polycarbonates or polyamides.

3. A method as claimed in claim 1, wherein the cholesteric liquid-crystalline polymer comprises
   a) at least one chiral bifunctional molecular structural unit with which a cholesteric liquid-crystalline phase having a pitch of less than 450 nm can be obtained and at least one further molecular unit selected from
   b) achiral compounds from the group consisting of aromatic hydroxycarboxylic acids, cycloaliphatic hydroxycarboxylic acids, aromatic aminocarboxylic acids and cycloaliphatic aminocarboxylic acids;
   c) achiral compounds from the group consisting of aromatic dicarboxylic acids and cycloaliphatic dicarboxylic acids,
   and
   d) achiral compounds from the group consisting of aromatic diols, cycloaliphatic diols, aromatic diamines and cycloaliphatic diamines.

4. A method as claimed in claim 1, wherein the cholesteric liquid-crystalline polymer comprises
   a) from 1 to 60 mol % of at least one chiral, bifunctional molecular unit;
   b) from 0 to 99 mol % of at least one achiral unit from the group consisting of aromatic hydroxycarboxylic acids, cycloaliphatic hydroxycarboxylic acids, aromatic aminocarboxylic acids and cycloaliphatic aminocarboxylic acids;
   c) from 0 to 49.5 mol % of at least one achiral unit from the group consisting of aromatic dicarboxylic acids and cycloaliphatic dicarboxylic acids, and
   d) from 0 to 99 mol % of at least one achiral unit from the group consisting of aromatic diols, cycloaliphatic diols, aromatic diamines and cycloaliphatic diamines,
   e) from 0 to 5 mol % of a branchable component having more than two functional groups, the sum of the individual components a) to e) being 100 mol %.

5. A method as claimed in claim 1, wherein the cholesteric liquid-crystalline polymer is applied in the form of photostable UV reflectors.

6. A method as claimed in claim 1, wherein the cholesteric liquid-crystalline polymer is applied in the form of UV stabilizers in cosmetic and pharmaceutical formulations.

7. A method as claimed in claim 1, wherein the cholesteric liquid-crystalline polymer is applied in the form of pigments.

8. A pigment comprising cholesteric liquid-crystalline polymers as defined in claim 1.

9. A pigment as claimed in claim 8, which is a multilayer pigment.

10. A cosmetic or pharmaceutical preparation comprising photoprotectants and intended for protecting the human epidermis or hair against UV light in the region from 280 to 400 nm, which in a cosmetically and pharmaceutically suitable carrier comprises cholesteric liquid-crystalline polymers as defined in claim 1 in amounts in which they are effective as photostable UV screens, alone or together with UV absorbers known per se for cosmetic and pharmaceutical preparations.

11. A cosmetic or pharmaceutical preparation as claimed in claim 10, comprising cholesteric liquid-crystalline polymers in the form of pigments as UV screens.

12. A cosmetic or pharmaceutical preparation as claimed in claim 10, comprising cholesteric liquid-crystalline polymers in the form of multilayer pigments as UV screens.

* * * * *